United States Patent [19]

Koshino et al.

[11] Patent Number: 5,194,423
[45] Date of Patent: Mar. 16, 1993

[54] ALPHA-(ALKYLCYCLOHEXYLOXY)-BETA-ALKANOLS AND PERFUME COMPOSITIONS CONTAINING THE SAME

[75] Inventors: Junji Koshino, Wakayama; Yoshiaki Fujikura, Utsunomiya; Nao Toi, Sakura; Rieko Yuki, Tokyo; Hajime Miyabe, Wakayama, all of Japan

[73] Assignee: Kao Corporation, Tokyo, Japan

[21] Appl. No.: 723,400

[22] Filed: Jun. 28, 1991

[30] Foreign Application Priority Data

Jul. 18, 1990 [JP] Japan .................. 2-187853
Apr. 5, 1991 [JP] Japan .................. 3-72648

[51] Int. Cl.$^5$ .................................. A61K 7/46
[52] U.S. Cl. ........................ 512/23; 568/664; 568/670
[58] Field of Search .............. 508/604, 670; 512/23

[56] References Cited

U.S. PATENT DOCUMENTS 4,757,051 7/1988 Gramlich et al. ............. 512/23

FOREIGN PATENT DOCUMENTS 0081699 6/1983 European Pat. Off. ........... 568/670
0419860 4/1991 European Pat. Off. ........... 568/670

OTHER PUBLICATIONS

Gora et al, Chem. Abst., vol. 111, #57,125i (1989).
Furuta et al., Tet. Letters, vol. 29, pp. 2215–2218 (1988).

*Primary Examiner*—James H. Reamer
*Attorney, Agent, or Firm*—Oblon, Spivak, McClelland, Maier & Neustadt

[57] ABSTRACT

An $\alpha$-(alkylcyclohexyloxy)-$\beta$-alkanol of formula (1)

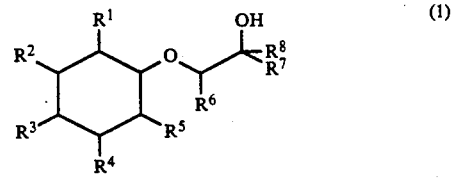

wherein at least one of $R^1$, $R^2$, $R^3$, $R^4$, and $R^5$ is the group

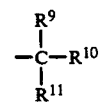

wherein $R^9$ and $R^{10}$ are the same or different alkyl groups having 1 to 4 carbon atoms or are coupled with each other to form a cycloalkyl group, and $R^{11}$ is a hydrogen atom or an alkyl group having 1 to 4 carbons or is a hydrogen atom when $R^9$ and $R^{10}$ form the cycloalkyl group, and the remaining $R^1$, $R^2$, $R^3$, $R^4$ and $R^5$ groups are hydrogen atoms or methyl groups, and wherein $R^6$, $R^7$ and $R^8$ are hydrogen atoms or the same or different alkyl groups having 1 to 6 carbon atoms.

4 Claims, No Drawings

ALPHA-(ALKYLCYCLOHEXYLOXY)-BETA-ALKANOLS AND PERFUME COMPOSITIONS CONTAINING THE SAME

BACKGROUND OF THE INVENTION

1. Field of the Invention

The present invention relates to a novel fragrance-imparting compound and more particularly to a compound with a woody or amber odor, having an excellent residual odor property, and a perfume composition containing the same.

2. Description of the Background

Perfumes having a residual odor property among perfumes having a woody or amber odor are used as a base note in compounding perfumes and are important materials for determining odors as a frame of compound perfumes. However, most of these compounds including natural materials are fairly expensive, which places a large restriction on the use of the materials in inexpensive compound perfumes. Hence, it is quite important to develop inexpensive materials having a woody or amber fragrance and a residual odor property.

It has been reported that ortho- and paraalkylcyclohexanols, ortho- and paraalkylcyclohexanones, ortho- and paraalkylcyclohexyl acetates, and the like, which are derived from alkylphenols and are represented by the following formulas,

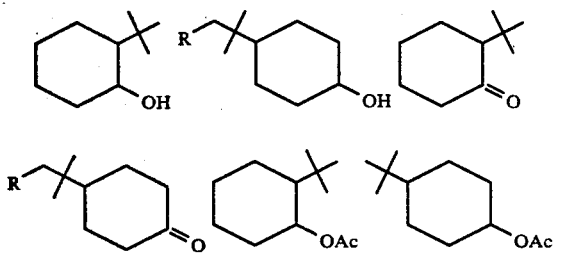

wherein R is a hydrogen atom or a methyl group, possess a woody odor. The compounds have been widely used as inexpensive materials, as disclosed in "Perfume and Flavor Chemicals", S. Arctander, Elizabeth (1969).

SUMMARY OF THE INVENTION

Accordingly, one object of the present invention is to provide a compound having a woody or amber odor and an excellent residual odor property.

Another object of the present invention is to provide a perfume composition containing a compound having a woody or amber odor and an excellent odor property Briefly, these objects and other objects of the present invention as hereinafter will become more readily apparent can be attained by an α-(alkylcyclohexyloxy)-β-alkanol of the formula (1)

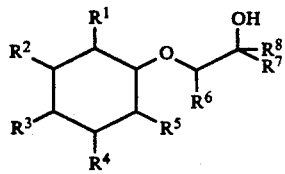

wherein at least one of $R^1$, $R^2$, $R^3$, $R^4$ and $R^5$ is the group

wherein $R^9$ and $R^{10}$ are either the same or different alkyl groups having 1 to 4 carbon atoms or are coupled with each other to form a cycloalkyl group, and $R^{11}$ is a hydrogen atom or an alkyl group having 1 to 4 carbons or is a hydrogen atom when $R^9$ and $R^{10}$ form the cycloalkyl group, and the remaining $R^1$, $R^2$, $R^3$, $R^4$ and $R^5$ groups are hydrogen atoms or methyl groups, and wherein $R^6$, $R^7$ and $R^8$ are hydrogen atoms or either the same or different alkyl groups having 1 to 6 carbon atoms.

In accordance with another aspect of the present invention, a perfume composition is provided which contains an α-(alkylcyclohexyloxy)-β-alkanol described above.

DETAILED DESCRIPTION OF THE PREFERRED EMBODIMENTS

The inventors have directed research effort and investigation into compounds which exhibit a woody or amber odor, which have an excellent residual odor property and which can be prepared at a low price. It has been found that cyclohexanes obtained by the hydrogenation of epoxide addition products of alkylcyclohexanols or alkylphenols satisfy such requirements. In formula (1) above, methyl, ethyl, n-propyl, iso-propyl, n-butyl, iso-butyl, tert-butyl, n-pentyl, n-hexyl and the like are examples of alkyl groups for $R^6$, $R^7$ and $R^8$. In these groups the alkyl groups having 1 to 4 carbon atoms in particular are preferred.

The present compounds of formula (1) can be prepared, for example, by any of the following reaction schemes.

(A) In the following scheme, alkylcyclohexanol (2) is treated in the presence of a strong base to make an alcoholate, and then the alcoholate is reacted with an epoxide (3) to prepare the product compound of formula (1).

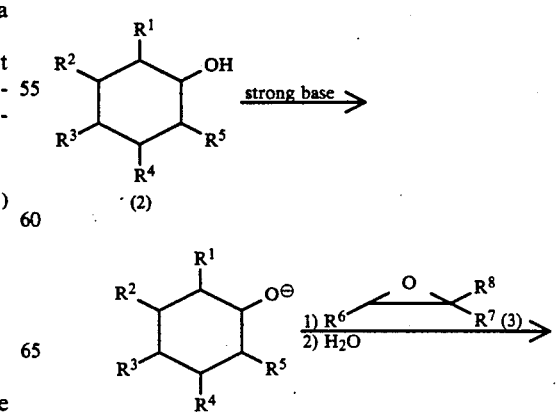

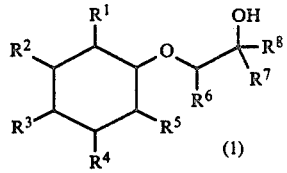

In the formulas, $R^1$ to $R^8$ are as defined above.

Solvents which are useful in the reaction include ether solvents such as diethyl ether, dibutyl ether, tetrahydrofuran and the like, and hydrocarbon solvents such as hexane, benzene, toluene, xylene and the like. Suitable strong bases which can be used include alkali metal hydrides such as sodium hydride, lithium hydride, potassium hydride and the like; alkali metal amides such as sodium amide, lithium amide, potassium amide and the like; alkali metals such as sodium, lithium, potassium and the like; and metal alkyl compounds such as alkyl lithium, alkyl magnesium halide and the like. The amount of the strong base used in the above reaction ranges from 0.1 to 2.0 equivalent per equivalent of alkylcyclohexanol (2), and a 1.0 to 1.2 equivalent amount is preferred in particular. The preferred amount of the epoxide (3) used in the above reaction is in a range of a 1.0 to 5.0 equivalent per equivalent of alkylcyclohexanol (2), and a 1.0 to 1.2 equivalent amount in particular is preferred. Both the alcoholate forming reaction and the epoxide addition reaction are carried out at a temperature of 30° to 120° C., preferably at 50° to 100° C.

In this case, when alkylcyclohexanol (2), as a raw material, is a mixture of cis-trans isomers, the compound (1) obtained is also a mixture of cis-trans isomers. The mixture of the isomers may be separated by, for example, column chromatography or the like, or can it be used as it is.

(B) In another embodiment, alkylphenol (4) is reacted with the epoxide (3) in the presence of a base catalyst to form α-(alkylphenyleneoxy)-β-alkanol (5), and the obtained compound (5) is hydrogenated in the presence of a metal catalyst to prepare present compound (1).

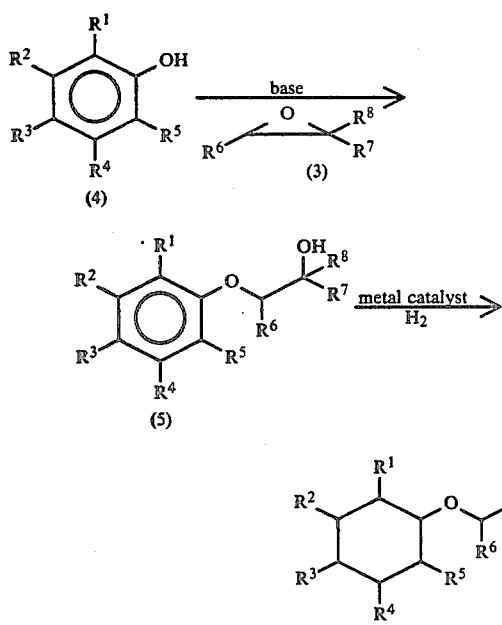

In the formulas, $R^1$ to $R^8$ are as defined above.

Suitable solvents which can be used in the above-described epoxide addition reaction include alcohol solvents such as methanol, ethanol, n-propanol, isopropanol and the like; ether solvents such as diethyl ether, dibutyl ether, tetrahydrofuran and the like; and hydrocarbon solvents such as hexane, benzene, toluene, xylene and the like. The reaction however, can also be carried out without using any solvent. Suitable examples of the base catalyst include alkali metal hydroxides such as sodium hydroxide, lithium hydroxide, potassium hydroxide and the like, and alkali metal carbonates such as sodium carbonate, lithium carbonate, potassium carbonate and the like. The bases can be used in powder form or as a solution containing the same. The amount of the base catalyst used in the above reaction is 0.01 to 2.0 equivalent per equivalent of alkylphenol (4), and 0.05 to 0.5 equivalent is preferred in particular. The amount of the epoxide (3) normally used in the above reaction is in a range of 1.0 to 5.0 equivalent per equivalent of alkylphenol (4), and 1.0 to 1.2 equivalent amount in particular is preferred. The epoxide addition reaction is carried out at a temperature of 30° to 200° C., preferably at 50° to 150° C.

Suitable solvents which can be used in the above-described hydrogenation reaction of the compound (5) include alcohol solvents such as methanol, ethanol, n-propanol, isopropanol and the like, and hydrocarbon solvents such as hexane, heptane, cyclohexane, methylcyclohexane and the like. However, the reaction can also be carried out without using any solvent. Suitable examples of the metal catalyst include palladium catalysts, ruthenium catalysts, rhodium catalysts, platinum catalysts, nickel catalysts and the like. The metal catalyst is used in the reaction in an amount ranging from 0.01 to 10% by weight relative to compound (5), and the range of 0.05 to 5% by weight is preferred. The hydrogenation reaction is carried out at a temperature of 50° to 300° C., preferably at 100° to 250° C. The pressure of the hydrogen in this reaction is a range of 1 to 150 atms, preferably a range of 10 to 100 atms.

Compound (1) in the form of a mixture of cis-trans isomers is formed by the hydrogenation of compound (5). The mixture of the isomers may be separated by, for example, column chromatography or the like, or it can be used as it is.

Embodiments of the present compound (1) include those having the following structure:

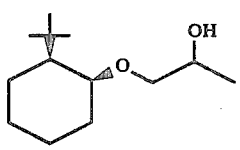

(1)

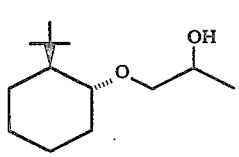

(2)

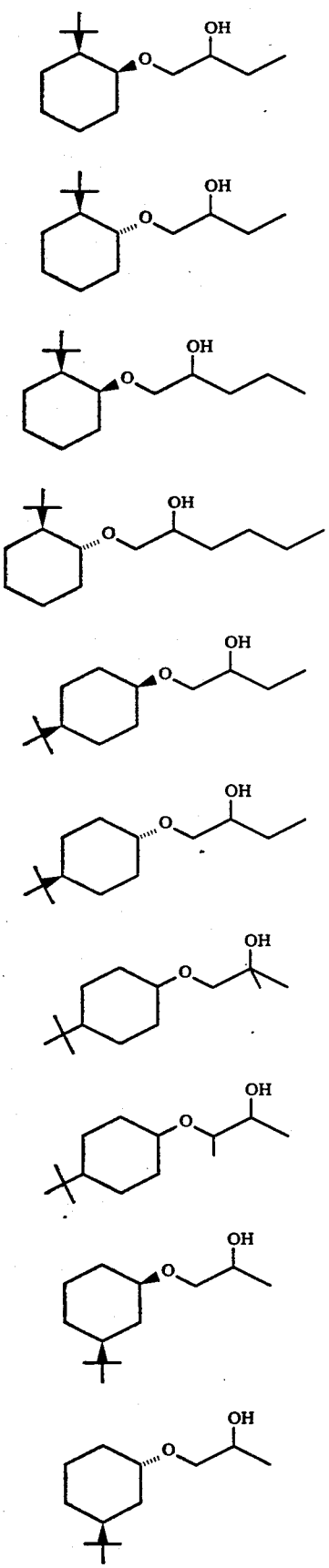
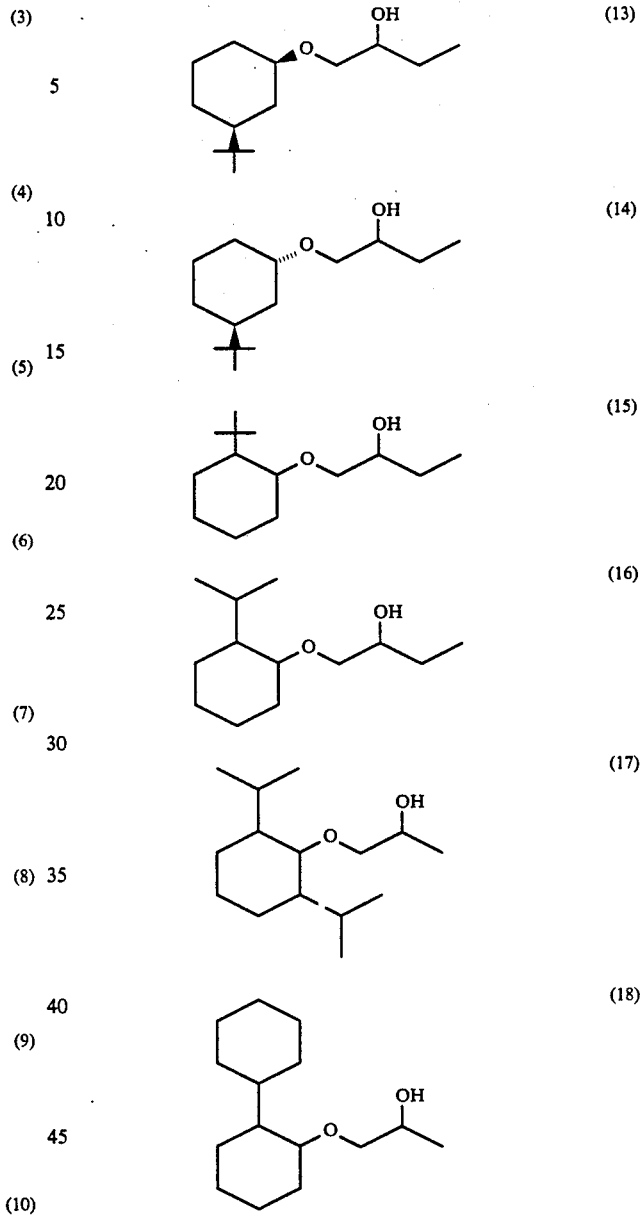

The odors of these compounds of the present invention are tabulated as follows.

| Compound No. | Odor | Residual Odor Property (days)** |
|---|---|---|
| (1) | woody, amber, minty | 3 |
| (2) | woody, amber, camphor | 3 |
| (3) | woody, amber, hay | 7 |
| (4) | woody, camphor, earthy, amber | 7 |
| (5) | woody, sandalwoody | 14 |
| (6) | woody | 14 |
| (7) | woody, sandalwoody, rose | 7 |
| (8) | woody | 7 |
| (9) | woody, amber, green | 7 |
| (10) | woody, green | 7 |
| (11) | woody | 3 |
| (12) | woody | 3 |
| (13) | woody | 7 |
| (14) | woody, sandalwoody | 7 |
| (15) | woody, amber, earthy | 14 |
| (16) | woody, amber, balsamic | 3 |

| Compound No. | Odor | Residual Odor Property (days)** |
|---|---|---|
| (17) | woody, amber | 14 |
| (18) | woody, styrax | 14 |

**Compound is applied to odor paper and the number of days the odor persists is measured.

As described above, the present compounds of formula (1) can be produced by using inexpensive materials and the present compounds having a woody or amber odor possess an excellent residual odor property. Hence, by blending the present compound (1), as a base note, with other odorants, an excellent perfume composition can be obtained. The amount of the present compound (1), blended into the likes of perfume compositions, varies depending on other compounded perfume ingredients, destination odors, and the like and is not limited provided that a woody or amber fragrance can be imparted. Further, the perfume compositions of the present invention can be widely used as a fragrance imparting component for perfumes, soaps, shampoos, rinses, detergents, cosmetics, fragrance imparting agents, and so forth either independently or in combination with other perfume compositions.

Having now generally described this invention, a further understanding can be obtained by reference to certain specific examples which are provided herein for purposes of illustration only and are not intended to be limiting unless otherwise specified.

EXAMPLES

EXAMPLE 1

Synthesis of 1-(2-tert-butylcyclohexyloxy)-2-propanol:
[Compounds (1) and (2)]

To a 300 ml round bottom flask provided with a Dimroth condenser and a dropping funnel, 7.5 g (0.194 mol) of sodium hydride (62 weight % mineral oil dispersion type) and 30 ml of tetrahydrofuran were added and heated at 60° C. under a nitrogen gas flow. Then, to this solution a mixture of 30.0 g (0.192 mol) of 2-tert-butylcyclohexanol (cis:trans=8:2) and 30 ml of tetrahydrofuran was added dropwise in approximately 30 minutes, and the mixed solution was stirred under reflux for 24 hours until the generation of hydrogen gas had stopped. The reacted mixed solution was cooled to 40° C., and after dropwise adding 11.1 g (0.192 mol) of propyleneoxide to the mixed solution, the solution was further stirred under reflux for 48 hours. The mixed solution was neutralized by 3N hydrochloric acid, and the organic layer was separated from the water layer. Distillation was then conducted and 9.9 g of 2-tert-butylcyclohexanol and 24.2 g of 1-(2-tert-butylcyclohexyloxy)-2-propanol (cis:trans=8:2) (bp. 112° to 113° C./5 mm Hg) were obtained in a 59% yield. Further, the cis-trans isomers of 1-(2-tert-butylcyclohexyloxy)-2-propanol were separated from each other by column chromatography using a developing solvent composed of Kieselgel 60 (trademark) of Merck Corporation and hexane:ethyl acetate =95:5.

1-(cis-2-tert-butylcyclohexyloxy)-2-propanol:
[Compound (1)]
IR (film, cm$^{-1}$): 905, 966, 1089, 1146, 1195, 1368, 2866, 2938, 3406
NMR (60 MHz, CDCl$_3$, ppm): 0.95 (s, 9H , 1.16 (d, J=7Hz, 3H), 1.2–2.0 (m, 8H), 2.1–2.5(m, 2H), 2.8–3.6 (m, 2H), 3.6–4.2 (m, 2H)
GC-MS(M+): 214

1-(trans-2-tert-butylcyclohexyloxy)-2-propanol:
[Compound (2)]
IR (film, cm$^{-1}$): 975, 1095, 1371, 1452, 2866, 2932, 3206
NMR (60 MHz, CDCl$_3$, ppm): 0.98 (s, 9H), 1.15 (d, J=7Hz, 3H), 1.1–2.4 (m, 10H), 2.9–4.2 (m, 4H)
GC-MS(M+): 214

EXAMPLE 2

Synthesis of 1-(2-tert-butylcyclohexyloxy)-2-butanol:
[Compounds (3) and (4)]

The synthesis was carried out in the same manner as described in Example 1, except that 13.8 g (0.192 mol) of 1,2-butyleneoxide was used instead of 11.1 g (0.192 mol) of propyleneoxide, to obtain 12.3 g of 2-tert-butylcyclohexanol and 24.1 g of 1-(2-tert-butylcyclohexyloxy)-2-butanol (cis:trans=8:2 bp. 122° to 123° C./5 mm Hg) in a 55% yield. Then, the cis-trans isomers of 1-(2-tert-butylcyclohexyloxy)-2-butanol were separated from each other in the same manner as described in Example 1.

1-(cis-2-tert-butylcyclohexyloxy)-2-butanol:
[Compound (3)]
IR (film, cm$^{-1}$): 890, 960, 1089, 1180, 1365, 1464, 2855, 2932, 3424
NMR (60 MHz, CDCl$_3$, ppm): 0.93 s, 9H), 0.97 t, J=7Hz, 3H), 1.0–2.0 (m, 10H), 2.0–2.4 (m, 2H), 3.0–3.9 (m, 4H)
GC-MS(M+): 228

1-(trans-2-tert-butylcyclohexyloxy)-2-butanol:
[Compound (4)]
IR (film, cm$^{-1}$): 972, 1095, 1368, 1452, 2866, 2932, 3448
NMR (60 MHz, CDCl$_3$, ppm): 0.93 (s and t, J=7Hz, 9H and 3H), 1.0–1.9 (m, 10H), 2.0–2.4 m, 2H), 3.0–3.8 (m, 4H)
GC-MS(M+): 228

EXAMPLE 3

Synthesis of 1-(2-tert-butylcyclohexyloxy)-2-butanol:
[Compounds (3) and (4)]

(a) To a 300 ml round bottom flask provided with a Dimroth condenser and a dropping funnel, 35 g of 48 weight % sodium hydroxide solution and 350 g (2.33 mol) of 2-tertbutylphenol were added and heated at 80° C. under a nitrogen gas flow atmosphere. Then, to this solution 176 g (2.45 mol) of 1,2-butyleneoxide was added dropwise in approximately 2 hours, and the mixed solution was stirred at 80° C. for 5 hours. After cooling the reacted mixed solution, the lower sodium hydroxide solution layer was separated from the organic layer. Distillation was then conducted and 497 g of 1-(2-tert-butylphenyloxy)-2-butanol (bp. 130° C./4 mm Hg) were obtained in a 96% yield.

1-(2-tert-butylphenyloxy)-2-butanol:
[Compound (5a)]
IR (film, cm$^{-1}$): 744, 975, 1038, 1092, 1134, 1233, 1290, 1362, 1392, 1443, 1491, 1599, 2956, 3058, 3412
NMR (60 MHz, CDCl$_3$, ppm): 1.07 (t, J=7Hz, 3H), 1.40 (s, 9H), 1.5–1.8 (m, 2H), 2.15, (α, J=4Hz, 1H), 3.8–4.1 (m, 3H), 6.8–7.4 (m, 4H)
GC-MS(M+): 222

(b) To a 500 ml autoclave, 50 g (0.23 mol) of 1-(2-tert-butylphenyloxy)-2-butanol, 150 g of isopropanol and 1.0 g of 5 weight % palladium catalyst supported on active carbon containing 50 weight % water (produced by N. E. Chemcat Co.) were added, and the mixture obtained was reacted at 190° C. at a hydrogen pressure of 70 kg/cm$^2$ for 27 hours until absorption of hydrogen had stopped. After the reaction was finished, the catalyst was filtered to remove it, and the reacted solution was distilled and 38.8 g of 1-(2-tert-butylcyclohexyloxy)-2-butanol (cis:trans=63:37) were obtained in a 74% yield of product.

EXAMPLE 4

Synthesis of 1-(2-tert-butylcyclohexyloxy)-2-hexanol: [Compounds 5) and (6)]

The synthesis was carried out in the same manner as described in Example 1, except that 19.2 g (0.192 mol) of 1,2-hexeneoxide was used instead of 11.1 g (0.192 mol) of propyleneoxide, 12.9 g of 2-tert-butylcyclohexanol and 26.5 g of 1-(2-tert-butylcyclohexyloxy)-2-hexanol (cis:trans=8:2) (bp. 116° to 117° C./1 mm Hg) were obtained in a 54% yield. Then, the cis-trans isomers of 1-(2-tert-butylcyclohexyloxy)-2-hexanol were separated from each other in the same manner as described in Example 1.

1-(cis-2-tert-butylcyclohexyloxy)-2-hexanol: [Compound (5)]

IR (film, cm$^{-1}$): 890, 960, 1089, 1176, 1365, 1464, 2860, 2932, 3430

NMR (60 MHz, CDCl$_3$, ppm): 0.93 (br.s, 12H), 1.1–2.5 (m, 16H), 2.9–3.6 (m, 2H), 3.6–4.0 (m, 2H)

GC-MS(M+): 256

1-(trans-2-tert-butylcyclohexyloxy)-2-hexanol: [Compound (6)]

IR (film, cm$^{-1}$): 970, 1098, 1368, 1452, 2866, 2932, 3466

NMR (60 MHz, CDCl$_3$, ppm): 0.97 (br.s, 12H), 1.1–2.5 (m, 16H), 1.0–1.9 (m, 10H), 2.9–3.6 (m, 2H), 3.6–4.0 (m, 2H)

GC-MS(M+): 256

EXAMPLE 5

Synthesis of 1-(4-tert-butylcyclohexyloxy)-2-butanol: [Compounds (7) and (8)]

The synthesis was carried out in the same manner as described in Example 1, except that 30.0 g (0.192 mol) of 4-tert-butylcyclohexanol (cis:trans=8:2) and 13.8 g (0.192 mol) of 1,2-butyleneoxide was used instead of 30.0 g (0.192 mol) of 2-tert-butylcyclohexanol (cis:trans=8:2) and 11.1 g (0.192 mol) of propyleneoxide. 9.6 g of 4-tert-butylcyclohexanol and 17.9 g of 1-(4-tert-butylcyclohexyloxy)-2-butanol (cis:trans=8:2) (bp. 130° to 133° C./5 mm Hg) were obtained in a 41% yield. Then, the cis-trans isomers of 1-(4-tert-butylcyclohexyloxy)-2-butanol were separated from each other in the same manner as described in Example 1.

1-(cis-4-tert-butylcyclohexyloxy)-2-butanol: [Compound (7)]

IR (film, cm$^{-1}$): 1032, 1092, 1116, 1182, 1368, 1470, 2872, 2944, 3470

NMR (60 MHz, CDCl$_3$, ppm): 0.87 (s, 9H), 0.97 (t, J=7Hz, 3H), 1.0–1.8 (m, 8H), 1.8–2.4 (M, 4H), 3.2–3.9 (m, 4H)

GC-MS(M+): 228

1-(trans-4-tert-butylcyclohexyloxy)-2-butanol: [Compound (8)]

IR (film, cm$^{-1}$): 1030, 1104, 1368, 1458, 2870, 2938, 3466

NMR (60 MHz, CDCl$_3$, ppm): 0.87 (s, 9H), 0.97 (t, J=7Hz, 3H), 1.0–2.4 (m, 12H), 3.0–3.8 (m, 4H)

GC-MS(M+): 228

EXAMPLE 6

Synthesis of 1-(4-tert-butylcyclohexyloxy)-2-methyl-2 propanol: [Compound (9)]

The synthesis was carried out in the same manner as described in Example 1, except that 20.0 g (0.128 mol) of 4-tert-butylcyclohexanol (cis:trans=4:6) and 8.8 g (0.128 mol) of 2-methylpropionoxide were used instead of 30.0 g (0.192 mol) of 2-tert-butylcyclohexanol (cis:trans=8:2) and 11.1 g (0.192 mol) of propyleneoxide. 6.2 g of 4-tert-butylcyclohexanol and 14.6 g of 1-(4-tert-butylcyclohexyloxy)-2-methyl-2-propanol (cis:trans=4:6) were obtained in a 50% yield.

1-(4-tert-butylcyclohexyloxy)-2-methyl-2-propanol (cis:trans=4:6): [Compound (9)]

IR (film, cm$^{-1}$): 918, 1098, 1368, 1470, 2938, 3448,

NMR (200 MHz, CDCl$_3$, ppm): 0.84 (s, 9H), 1.03 (s, 3.6H), 1.06 (s, 2.4H), 0.8–2.2 (m, 9H), 2.42 (s, 0.6H), 2.55 (s, 0.4H), 3.1–3.3 (m, 1H), 3.19 (s, 0.8H), 3.28 (s, 1.2H)

GC-MS(M+): 228 (cis), 228 (trans)

EXAMPLE 7

Synthesis of 2-(4-tert-butylcyclohexyloxy)-3-butanol: [Compound (10)]

The synthesis was carried out in the same manner as described in Example 1, except that 20.0 g (0.128 mol) of 4-tert-butylcyclohexanol (cis:trans=4:6) and 8.8 g (0.128 mol) of 2,3-butyleneoxide were used instead of 30.0 g (0.192 mol) of 2-tert-butylcyclohexanol (cis:trans=8:2) and 11.1 g (0.192 mol) of propyleneoxide. 11.2 g of 4-tert-butylcyclohexanol and 9.3 g of 2-(4-tert-butylcyclohexyloxy)-3-butanol (a mixture of cis-trans and threo-erythro isomers) were obtained in a 32% yield.

2-(4-tert-butylcyclohexyloxy)-3-butanol: [Compound (10)]

IR (film, cm$^{-1}$): 912, 969, 1098, 1158, 1260, 1320, 1368, 1446, 2938, 3424

NMR (200 MHz, CDCl$_3$, ppm): 0.87 (s, 9H), 1.08 (d, J=7Hz, 3H), 1.12 (d, J=7Hz, 3H), 0.9–2.0 (m, 9H), 2.32 (br d, J=3.5Hz, 1H), 3.5–3.7 (m, 1H), 3.7–3.9 (m, 1H)

GC-MS(M+): 228

EXAMPLE 8

Synthesis of 1-(3-tert-butylcyclohexyloxy)-2-propanol: [Compounds (11) and (12)]

The synthesis was carried out in the same manner as described in Example 1, except that 30.0 g (0.192 mol) of 3-tert-butylcyclohexanol (cis:trans=2:8) was used instead of 30.0 g (0.192 mol) of 2-tert-butylcyclohexanol (cis:trans=8:2). 10.2 g of 3-tert-butylcyclohexanol and 15.2 g of 1-(3-tert-butylcyclohexyloxy)-2-propanol (cis:trans=2:8) (bp. 135° to 138° C./9 mm Hg) were obtained in a 37% yield. Then, the cis-trans isomers of 1-(3-tert-butylcyclohexyloxy)-2-propanol were separated from each other in the same manner as described in Example 1.

1-(cis-3-tert-butylcyclohexyloxy)-2-propanol: [Compound (11)]

IR (film, cm$^{-1}$): 963, 1089, 1368, 1392, 1452, 2938, 3424

NMR (200 MHz, CDCl$_3$, ppm): 0.83 (s, 9H), 1.00 (d, J=7 Hz, 3H), 0.8-2.1 (m, 9H), 2.61 (s, 1H), 3.1-3.2 ((m, 1H), 3.3-3.4 (m, 1H), 3.69 (s, 1H), 3.92 (br.s, 1H)

GC-MS(M+): 214

1-(trans-3-tert-butylcyclohexyloxy)-2-propanol:
[Compound (12)]

IR (film, cm$^{-1}$): 966, 1095, 1368, 1395, 1464, 2938, 3448

NMR (200 MHz, CDCl$_3$, ppm): 0.86 (s, 9H), 1.00 (t, J=7Hz, 3H), 0.8-2.2 (m, 9H), 2.5 (s, 1H), 3.1-3.3 (m, 2H), 3.4-3.6 (m, 1H), 3.91 (br.s, 1H)

GC-MS(M+): 214

EXAMPLE 9

Synthesis of 1-(3-tert-butylcyclohexyloxy)-2-butanol:
[Compounds (13) and (14)]

The synthesis was carried out in the same manner as described in Example 1, except that 30.0 g (0.192 mol) of 3-tert-butylcyclohexanol (cis:trans=2:8) and 13.8 g (0.192 mol) of 1,2-butyleneoxide were used instead of 30.0 g (0.192 mol) of 2-tert-butylcyclohexanol (cis:-trans=8:2) and 11.1 g (0.192 mol) of propyleneoxide. 11.3 g of 3-tert-butylcyclohexanol and 9.3 g of 1-(3-tert-butylcyclohexyloxy)-2-butanol (cis:trans=2:8) (bp. 145° to 148° C./10 mm Hg) were obtained in a 32% yield. Then, the cis-trans isomers of 1-(3-tert-butylcyclohexyloxy)-2-butanol were separated from each other in the same manner as described in Example 1.

1-(cis-3-tert-butylcyclohexyloxy)-2-butanol:
[Compound (13)]

IR (film, cm$^{-1}$): 1095, 1368, 1464, 2938, 3454

NMR (200 MHz, CDCl$_3$, ppm): 0.83 (s, 9H), 0.97 (t, J=7Hz, 3H), 0.8-2.1 (m, 11H), 2.50 (s, 1H), 3.1-3 3 (m, 1H), 3.4-3.5 (m, 1H), 3.69 (br.s, 2H)

GC-MS(M+): 228

1-(trans-3-tert-butylcyclohexyloxy)-2-butanol:
[Compound (14)]

IR (film, cm$^{-1}$): 1095, 1368, 1464, 2938, 3454

NMR (200 MHz, CDCl$_3$, ppm): 0.86 (s, 9H), 0.97 (t, J=7HZ, 3H), 0.8-1.9 (m, 9H), 2.06 (br.s, 2H), 2.42 (s, 1H), 3.1-3.4 (m, 2H), 3.4-3.6 (m, 1H), 3.6-3.8 (m, 1H)

GC-MS(M+): 228

EXAMPLE 10

Synthesis of 1-(2-tert-butyl-5-methylcyclohexyloxy)-2-butanol:
[Compound (15)]

(a) The synthesis was carried out in the same manner as described in Example 3a, except that 382 g (2.33 mol) of 2-tert-butyl-5-methylphenol was used instead of 350 g (2.33 mol) of 2-tert-butylphenol. 522 g of 1-(2-tert-butyl-5-methylphenyloxy)-2-butanol (bp. 139° to 140° C./3.5 mm Hg) were obtained in a 95% yield.

1-(2-tert-butyl-5-methylphenyloxy)-2-butanol:

IR (film, cm$^{-1}$): 808, 1042, 1086, 1144, 1182, 1258, 1294, 1410, 1460, 1502, 1612, 2960, 3404

NMR (200 MHz, CDCl$_3$, ppm) 1.07 (t, J=7Hz, 3H), 1.39 (s, 9H), 1.5-1.8 (m, 2H), 2.14 (d, J=4Hz, 1H), 2.31 (s, 3H), 3.8-4.1 (m, 3H), 6.6-7.3 (m, 3H)

GC-MS(M+): 236

(b) The synthesis was carried out in the same manner as described in Example 3b, except that 50 g (0.21 mol) of 1-(2-tert-butyl-5-methylphenyloxy)-2-butanol were used instead of 50 g (0.23 mol) of 1-(2-tert-butylphenyloxy)-2-butanol and the amount of the same palladium catalyst was increased to 2.5 g to effect the reaction for 4 hours, to obtain 32 g of 1-(2-tert-butyl-5-methylcyclohexyloxy)-2-butanol (bp. 139° to 140° C./3.5 mm Hg) in a 63% yield.

1-(2-tert-butyl-5-methylcyclohexyloxy)-2-butanol:
[Compound (15)]

IR (film, cm$^{-1}$): 1086, 1365, 1461, 2950, 3448

NMR (200 MHz, CDCl$_3$, ppm): 0.94 (s, 9H), 0.8-2.4 (m, 15H), 2.9-3.8 (m, 4H)

GC-MS(M+): 242

EXAMPLE 11

Synthesis of 1-(2-isopropylcyclohexyloxy)-2-butanol:
[Compound (16)]

The synthesis was carried out in the same manner as described in Example 1, except that 20.0 g (0.141 mol) of 2-isopropylcyclohexanol (cis:trans=6:4) and 10.1 g (0.141 mol) of 1,2-butyleneoxide were used instead of 30.0 g (0.192 mol) of 2-tert-butylcyclohexanol (cis:-trans=8:2) and 11.1 g (0.192 mol) of propyleneoxide. 6.5 g of 2-isopropylcyclohexanol and 16.6 g of 1-(2-isopropylcyclohexyloxy)-2-butanol (cis:trans=6:4) were obtained in a 55% yield.

1-(2-isopropylcyclohexyloxy)-2-butanol:
[Compound (16)]

IR (film, cm$^{-1}$): 963, 981, 1092, 1140, 1200, 1386, 1461, 2926, 3424

NMR (200 MHz, CDCl$_3$, ppm): 0.90 (d, J=7Hz, Ca3H), 0.92 (d, J=7Hz, Ca3H), 0.98 (t, J=7Hz, 3H), 0.8-1.9 (m, 11H), 1.9-2.2 (m, 1H), 2.3-2.6 (m, 1H), 2.9-3.8 (m, 3H)

GC-MS(M+): 214

EXAMPLE 12

Synthesis of 1-(2,6-diisopropylcyclohexyloxy)-2-propanol:
[Compound (17)]

(a) The synthesis was carried out in the same manner as described in Example 3a, except that 50.0 g (0.28 mol) of 2,6-diisopropylphenol and 22.0 g (0.31 mol) of propyleneoxide were used instead of 350 g (2.33 mol) of 2-tert-butylphenol and 176 g (2.45 mol) of 1,2-butyleneoxide. 59.5 g of 1-(2,6-diisopropylphenyloxy)-2-propanol (bp. 138° C./5 mm Hg) were obtained in a 90% yield.

1-(2,6-diisopropylphenyloxy)-2-propanol:

IR (film, cm$^{-1}$): 756, 798, 1020, 1047, 1185, 1254, 1323, 1446, 2866, 2962, 3064, 3406

NMR (200 MHz, CDCl$_3$, ppm): 1.24 (d, J=7Hz, 12H), 1.28 (d, J=7 Hz, 3H), 2.57 (br.s, 1H), 3.31 (scp, J=7 Hz, 2H), 3.5-3.9 (m, 2H), 4.1-4.4 1H), 2.31 (s, 3H), 3.8-4.1 (m, 3H), (m, 1H), 7.11 (s, 3H)

GC-MS(M+): 236

(b) The synthesis was carried out in the same manner as described in Example 3b, except that 30 g (0.13 mol) of 1-(2,6-diisopropylphenyloxy)-2-propanol were used instead of 50 g (0.23 mol) of 1-(2-tert-butylphenyloxy)-2-butanol and the amount of the same palladium catalyst was increased to 1.5 g. The reaction was carried out for 5 hours and 21 g of 1-(2,6-diisopropylcyclohexyloxy)-2-propanol were obtained in a 67% yield.

1-(2,6-diisopropylcyclohexyloxy)-2-propanol:
[Compound (17)]

IR (film, cm$^{-1}$): 960, 1095, 1158, 1371, 1386, 1470, 2944, 3406

NMR (200 MHz, CDCl$_3$, ppm): 0.8-1.1 (m, 12H), 1.13 (d, J=7Hz, 3H), 1.1-1.9 (m, 10H), 2.53 (d, J=3Hz, 1H), 3.2-4.1 (m, 4H)

GC-MS(M+): 242

EXAMPLE 13

Synthesis of 1-(2-cyclohexylcyclohexyloxy)-2-propanol:

[Compound (18)]

The synthesis was carried out in the same manner as described in Example 1, except that 34.9 g (0.192 mol) of 2-cyclohexylcyclohexanol (cis:trans=8:2) was used instead of 30.0 g (0.192 mol) of 2-tert-butylcyclohexanol (cis:trans=8:2). 10.4 g of 2-cyclohexylcyclohexanol and 24.9 g of 1-(2-cyclohexylcyclohexyloxy)-2-propanol were obtained in a 54% yield.

1-(2-cyclohexylcyclohexyloxy)-2-propanol:

[Compound (18)]

IR film, cm$^{-1}$: 963, 1092, 1143, 1260, 1317, 1338, 1368, 1449, 2848, 2932, 3406

NMR (200 MHz, CDCl$_3$, ppm): 1.16 (d, J=7Hz, 3H), 0.8–2.1 (m, 20H), 2.52 (d, J=2.4Hz, 1H), 2.94 (dd, J=8.7Hz and J=8.7Hz, 1H), 3.57 (dd, J=8.7Hz and J=2.4Hz, 1H), 3.6 3.7 (m, 1H), 3.8–4.0 (m, 1H)

GC-MS(M+): 240

EXAMPLE 14

| Chypre-type Perfume Composition | |
| --- | --- |
| | Parts by weight |
| Bergamot oil | 100 |
| Rose base | 100 |
| Methyldihydrojasmonate | 100 |
| Lirhal *1 | 100 |
| Eugenol | 20 |
| Benzyl salicylate | 50 |
| cis-3-hexenyl salicylate | 30 |
| γ-Methyl inone | 50 |
| Vetiver oil | 20 |
| Sandalmysolcore *2 | 10 |
| Patchouli oil | 100 |
| Musk ketone | 50 |
| Amber base | 50 |
| Acetylcedrene | 100 |
| Total | 880 |

*1: Trademark of IFF Co.; 4-(4-hydroxy-4-methyl-pentyl)-3-cyclohexen-1-carboxyaldehyde
*2: Trademark of Kao Chemicals Co., Ltd.; 2-methyl-4-(2,3,3-trimethyl-3-cyclopentene-1-yl)-2-butene-1-ol To 880 parts by weight of the above perfume composition 120 parts by weight of 1-(2-tert-butylcyclohexyloxy)-2-butanol of the present invention was added to obtain a chypre-type perfume composition having a mild odor with sweetness and bulkiness so as to wrap the wildness of the patchouli oil.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An α-(alkylcyclohexyloxy)-β-alkanol of formula (I):

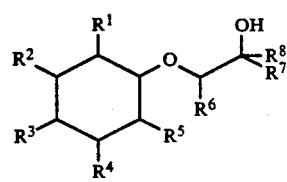

wherein at least one of substituents $R^1$, $R^2$, $R^3$, $R^4$ and $R^5$ is a tertiary alkyl group of 4–8 carbon atoms, and the remaining $R^1$, $R^2$, $R^3$, $R^4$ and $R^5$ groups are hydrogen atoms or methyl groups, and wherein $R^6$, $R^7$ and $R^8$ are hydrogen atoms or the same or different alkyl groups having 1–6 carbon atoms, with the proviso that $R^6$, $R^7$ and $R^8$ are not all hydrogen atoms at the same time.

2. The compound of claim 1, wherein said compound is

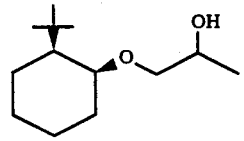  (1)

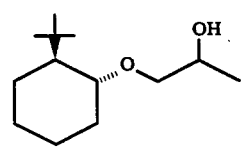  (2)

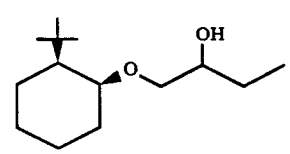  (3)

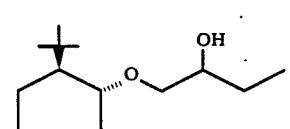  (4)

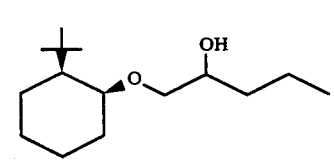  (5)

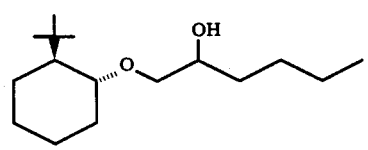  (6)

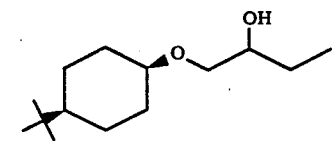  (7)

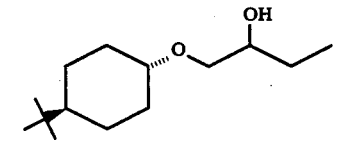  (8)

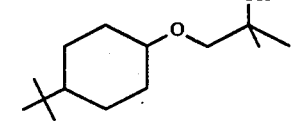  (9)

-continued

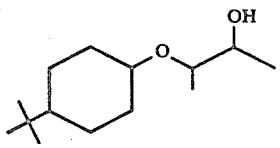 (10)

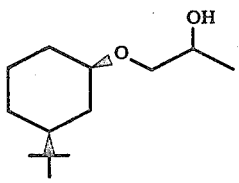 (11)

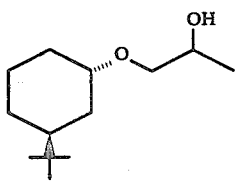 (12)

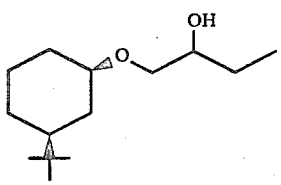 (13)

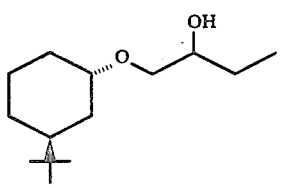 (14)

-continued

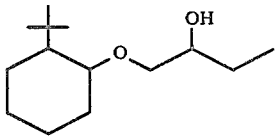 (15)

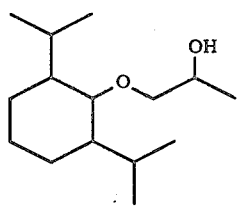 (17)

3. A perfume composition containing the α-(alkylcyclohexyloxy)-β-alkanol of claim 1 in combination with perfume composition auxiliaries.

4. An α-(alkylcyclohexyloxy)-β-alkanol of formula (I):

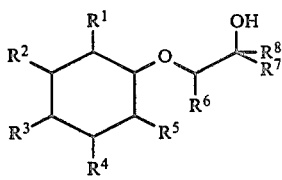

wherein at least one of substituents $R^1$, $R^2$, $R^3$, $R^4$ and $R^5$ is a tertiary alkyl group of 4-13 carbon atoms, and the remaining $R^1$, $R^2$, $R^3$, $R^4$ and $R^5$ groups are hydrogen atoms or methyl groups, and wherein $R^6$, $R^7$ and $R^8$ are hydrogen atoms or the same or different alkyl groups having 1-6 carbon atoms, with the proviso that $R^6$, $R^7$ and $R^8$ are not all hydrogen atoms at the same time.

* * * * *